(12) United States Patent
Inoue et al.

(10) Patent No.: US 10,646,174 B2
(45) Date of Patent: May 12, 2020

(54) IMAGING APPARATUS FOR DIAGNOSIS, METHOD OF CONTROLLING THE SAME, PROGRAM, AND COMPUTER READABLE STORAGE MEDIUM

(71) Applicant: TERUMO KABUSHIKI KAISHA, Shibuya-ku, Tokyo (JP)

(72) Inventors: Kouichi Inoue, Odawara (JP); Junya Furuichi, Hadano (JP); Hijiri Etou, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 921 days.

(21) Appl. No.: 14/865,532

(22) Filed: Sep. 25, 2015

(65) Prior Publication Data

US 2016/0015337 A1    Jan. 21, 2016

Related U.S. Application Data

(63) Continuation of application No. PCT/JP2013/002382, filed on Apr. 5, 2013.

(51) Int. Cl.
   *A61B 6/00* (2006.01)
   *A61B 8/12* (2006.01)
   (Continued)

(52) U.S. Cl.
   CPC .............. *A61B 6/12* (2013.01); *A61B 5/0035* (2013.01); *A61B 5/0066* (2013.01);
   (Continued)

(58) Field of Classification Search
   CPC . A61B 5/0035; A61B 5/0066; A61B 5/02007; A61B 5/7207; A61B 5/7246;
   (Continued)

(56) References Cited

U.S. PATENT DOCUMENTS

2005/0197559 A1    9/2005  Boese et al.
2006/0058647 A1    3/2006  Strommer et al.
(Continued)

FOREIGN PATENT DOCUMENTS

JP    11-056752 A    3/1999
JP    2005-253964 A    9/2005
(Continued)

OTHER PUBLICATIONS

Extended European Search Report dated Nov. 23, 2016, by the European Patent Office in corresponding European Application No. 13880878.7 (8 pages).
(Continued)

*Primary Examiner* — James M Kish
(74) *Attorney, Agent, or Firm* — Buchanan Ingersoll & Rooney PC

(57) ABSTRACT

An imaging apparatus and method for diagnosis acquiring information of an inside of a blood vessel and reconstructing a vascular image are disclosed, wherein when acquiring data through a rotation position and a movement of an imaging core, X-ray images at a fixed viewpoint position are synchronized so as to be continuously input along a time axis. Then, timing when vascular activity such as a cardiac beat can occur is determined based on the X-ray images. A plurality of vascular cross-sectional images on a plane orthogonal to a vascular axis acquired through the rotation and the movement of the imaging core are acquired. Then, a vascular image along the vascular axis is generated from the vascular cross-sectional image or the vascular cross-sectional images in series, and when performing a display, a site having vascular activity is displayed in a discriminable manner.

20 Claims, 11 Drawing Sheets

(51) Int. Cl.
*A61B 6/12* (2006.01)
*A61B 5/00* (2006.01)
*A61B 5/02* (2006.01)
*A61B 8/08* (2006.01)

(52) U.S. Cl.
CPC ........ *A61B 5/02007* (2013.01); *A61B 5/7207* (2013.01); *A61B 5/7289* (2013.01); *A61B 5/743* (2013.01); *A61B 6/463* (2013.01); *A61B 6/486* (2013.01); *A61B 6/504* (2013.01); *A61B 6/5217* (2013.01); *A61B 6/5247* (2013.01); *A61B 8/0891* (2013.01); *A61B 8/12* (2013.01); *A61B 8/5276* (2013.01); *A61B 5/7246* (2013.01)

(58) Field of Classification Search
CPC ......... A61B 5/7289; A61B 5/743; A61B 6/12; A61B 6/463; A61B 6/486; A61B 6/504; A61B 6/5217; A61B 6/5247; A61B 8/0891; A61B 8/12; A61B 8/5276
See application file for complete search history.

(56) References Cited

U.S. PATENT DOCUMENTS

| | | |
|---|---|---|
| 2007/0038081 A1 | 2/2007 | Eck et al. |
| 2008/0095421 A1 | 4/2008 | Sun et al. |
| 2008/0247621 A1 | 10/2008 | Zarkh et al. |
| 2011/0158488 A1 | 6/2011 | Cohen et al. |
| 2012/0059253 A1 | 3/2012 | Wang et al. |

FOREIGN PATENT DOCUMENTS

| | | |
|---|---|---|
| JP | 2006-204430 A | 8/2006 |
| JP | 2010-158288 A | 7/2010 |
| JP | 2010-253017 A | 11/2010 |

OTHER PUBLICATIONS

International Search Report (PCT/ISA/210) dated Jul. 16, 2013, by the Japanese Patent Office as the International Searching Authority for International Application No. PCT/JP2013/002382.

IMAGING APPARATUS FOR DIAGNOSIS, METHOD OF CONTROLLING THE SAME, PROGRAM, AND COMPUTER READABLE STORAGE MEDIUM

CROSS-REFERENCES TO RELATED APPLICATIONS

This application is a continuation of International Application No. PCT/JP2013/002382 filed on Apr. 5, 2013, the entire content of which is incorporated herein by reference.

TECHNICAL FIELD

The present disclosure relates to a technology of generating a tomographic image of a biological tissue by using light or ultrasounds ultrasound.

BACKGROUND DISCUSSION

Imaging apparatuses for diagnosis have been widely used to perform diagnoses of arteriosclerosis, and to perform preoperative diagnoses or to check postoperative results when intra-vascular treatment is performed using a high-performance catheter such as a balloon catheter and a stent.

The imaging apparatus for diagnosis can include an intra-vascular ultrasound apparatus for diagnosis (IVUS) and an optical coherence tomography apparatus for diagnosis (OCT), each of which has characteristics different from one another.

In addition, recently, an imaging apparatus for diagnosis (an imaging apparatus for diagnosis including an ultrasound transmitting and receiving unit which can transmit and receive ultrasound, and a light transmitting and receiving unit which can transmit and receive light) in which a function of the IVUS and a function of the OCT are combined together has been proposed (for example, refer to JP-A-11-56752 and JP-A-2006-204430).

The aforementioned imaging apparatus for diagnosis obtains tomographic images, which are orthogonal to the axis of a blood vessel. Therefore, a three-dimensional image can be generated by connecting the tomographic images in series. Once the three-dimensional image is generated, the tomographic image can be obtained at a free viewpoint and a free cross section.

Incidentally, a blood vessel which is positioned close to the heart, particularly, the coronary artery which is positioned so as to surround the heart is influenced by beating activities (hereinafter, simply referred to as "the cardiac beat") of the heart, and the position thereof changes. Even though the continuous tomographic images along a vascular axis of the blood vessel are obtained by the above-described imaging apparatus for diagnosis, when there is vascular activity, for example, a site influenced by a cardiac beat resulting in vascular activity and a site not influenced do not smoothly connect to each other, thereby exhibiting unnatural images. In a case of an experienced doctor, it may be understood that the unnatural site implies an occurrence of an influence of vascular activity such as a cardiac beat. However, it can be difficult for other ones to judge the state.

JP-A-2005-253964 discloses a known technology of detecting cardiac beating activity and correcting the image. According to the technology, a position sensor is provided inside a catheter and scanned (IVUS or OCT) images are recorded together with positions detected by the position sensor. A movement locus of the catheter can be confirmed when the catheter is internally equipped with the position sensor. However, it can be difficult to determine whether the locus is caused due to the shape of a blood vessel or such a movement locus occurs due to a cardiac beat.

SUMMARY

The present disclosure has been made in consideration of the above-described problems. In this description, a technology is disclosed, which displays a site having vascular activity and a site without thereof (for example, a site influenced by a cardiac beat and a site not influenced).

An imaging apparatus is disclosed for diagnosis acquiring information of an inside of a blood vessel and reconstructing a vascular image by using a probe that accommodates an imaging core which emits light or ultrasound toward a lumen surface of a blood vessel of an examinee and detects reflection of the light or ultrasound, so as to rotate the imaging core and to move the imaging core along the probe at a predetermined velocity, the apparatus including X-ray image acquisition means for continuously acquiring X-ray images of the examinee along a time axis while acquiring the information of the inside of the blood vessel by performing the rotation and the movement of the imaging core, specification means for specifying the vascular-activity occurrence X-ray image based on a degree of correlation of an adjacent X-ray image with respect to the time axis of the X-ray image which is acquired by the X-ray image acquisition means, determination means for determining a corresponding position of the moving imaging core for imaging timing of the X-ray image which is specified by the specification means, generation means for generating the axially-directed cross-sectional image along the vascular axis based on the information acquired through the rotation and the movement of the imaging core and display means for displaying a composite result of the axially-directed cross-sectional image which is generated by the generation means and an image which shows the position determined by the determination means.

According to an exemplary embodiment, when displaying a vascular image orthogonal to a vascular axis or a vascular image along the vascular axis, a site influenced by vascular activity (for example, a site which is estimated to be influenced by a cardiac beat) can be displayed in a discriminable manner.

Other features and advantages of the present disclosure will be clearly described below with reference to the accompanying drawings. In the accompanying drawings, the same reference numerals and signs will be applied to the same or similar constitutions.

BRIEF DESCRIPTION OF THE DRAWINGS

The accompanying drawings are incorporated in this disclosure, take part in the constitution, illustrate embodiments of the present disclosure, and are used to describe the principle of the present disclosure together with the disclosure thereof.

DETAILED DESCRIPTION

Hereinafter, embodiments of the present disclosure will be described in detail with reference to the accompanying drawings. In this disclosure, descriptions are given regarding exemplary embodiments and examples, which can be applied to an apparatus for acquiring an optical tomographic image. However, the embodiments can be applied to an apparatus, for example, which uses ultrasound or an apparatus which uses both light and ultrasound. Therefore, the present disclosure is not limited to the aforementioned point.

Figure 1:
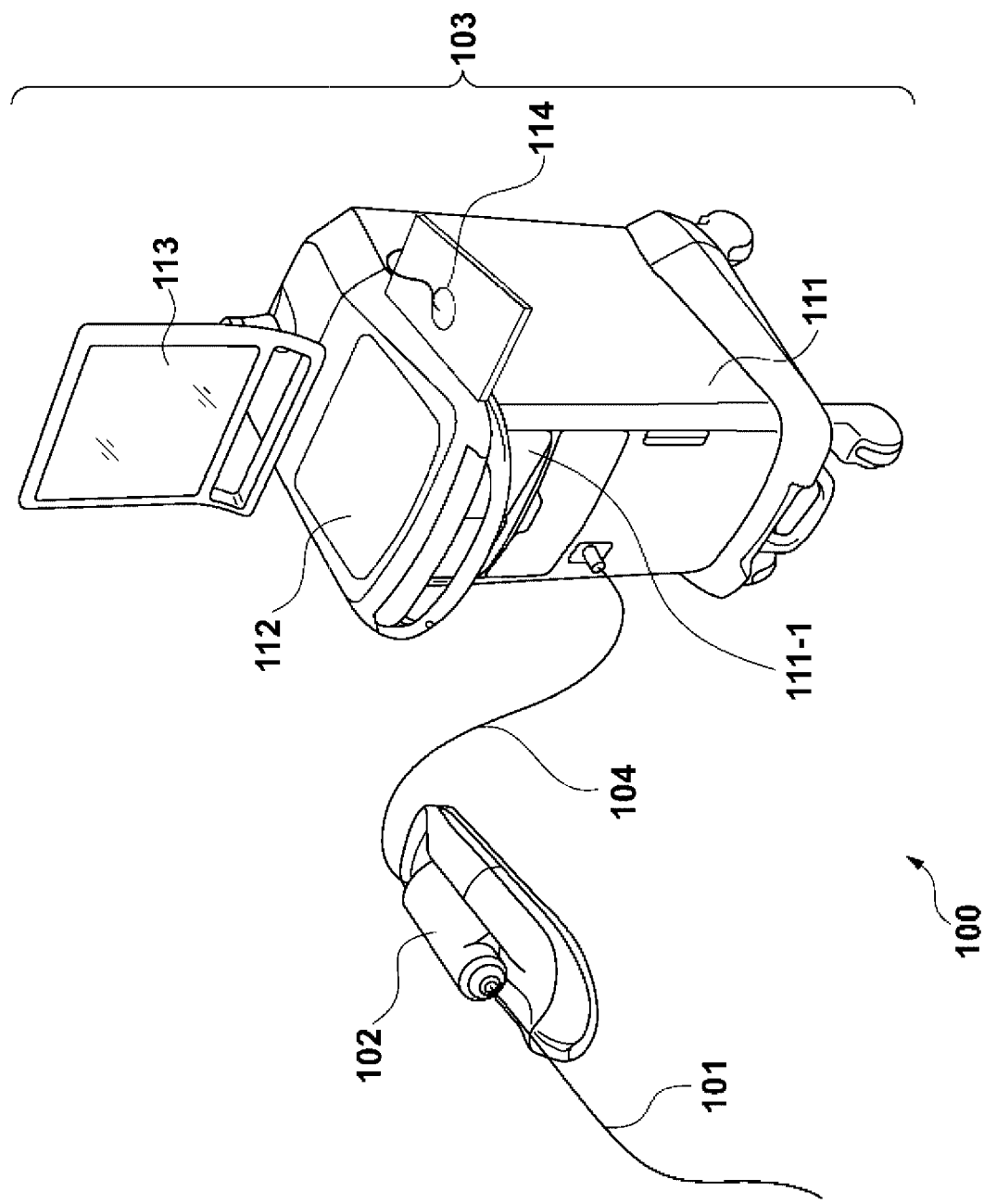
FIG. 1 is a diagram illustrating a constitution of the appearance of an imaging apparatus for diagnosis in accordance with an exemplary embodiment.

FIG. 1 is a diagram illustrating a constitution of the appearance of an imaging apparatus 100 for diagnosis according to an exemplary embodiment of the present disclosure.

As illustrated in FIG. 1, the imaging apparatus 100 for diagnosis can include a probe unit 101, a scanner and pull-back unit 102 and an operation control device 103. The scanner and pull-back unit 102 and the operation control device 103 are connected to each other through a signal wire 104 so as to be able to transfer various signals.

An imaging core which is directly inserted into a blood vessel is interpolated into the probe unit 101. The imaging core can include a light transmitting and receiving unit which continuously transmits transferred light (measurement light) into a blood vessel and continuously receives reflected light from the inside of the blood vessel. In the imaging apparatus 100 for diagnosis, the imaging core can be used to measure a state inside a blood vessel.

The probe unit 101 is attached to the scanner and pull-back unit 102 in a freely detachable manner. A built-in motor is driven so as to define axial motion inside a blood vessel and rotary motion around the axis of the imaging core which is interpolated into the probe unit 101.

The operation control device 103 can include a function of inputting various setting values when performing measurement and a function of processing data obtained through the measurement and displaying various images of a blood vessel.

In the operation control device 103, the reference numeral 111 indicates a main body control unit. The main body control unit 111 causes reflected light obtained through the measurement to interfere with reference light obtained by separating light from a light source, thereby generating interference light data, and the main body control unit 111 performs processing of line data generated based on the interference light data, thereby generating a vascular cross-sectional image (a radially-directed cross-sectional image).

The reference numeral 111-1 indicates a printer and DVD recorder, which prints a processing result of the main body control unit 111 and stores the processing result as data. The reference numeral 112 indicates an operation panel, and a user inputs various setting values and instructions via the operation panel 112. The reference numeral 113 indicates an LCD monitor as a display device, which displays a cross-sectional image generated in the main body control unit 111. The reference numeral 114 indicates a mouse, which is a pointing device (a coordinate input device).

Figure 2:
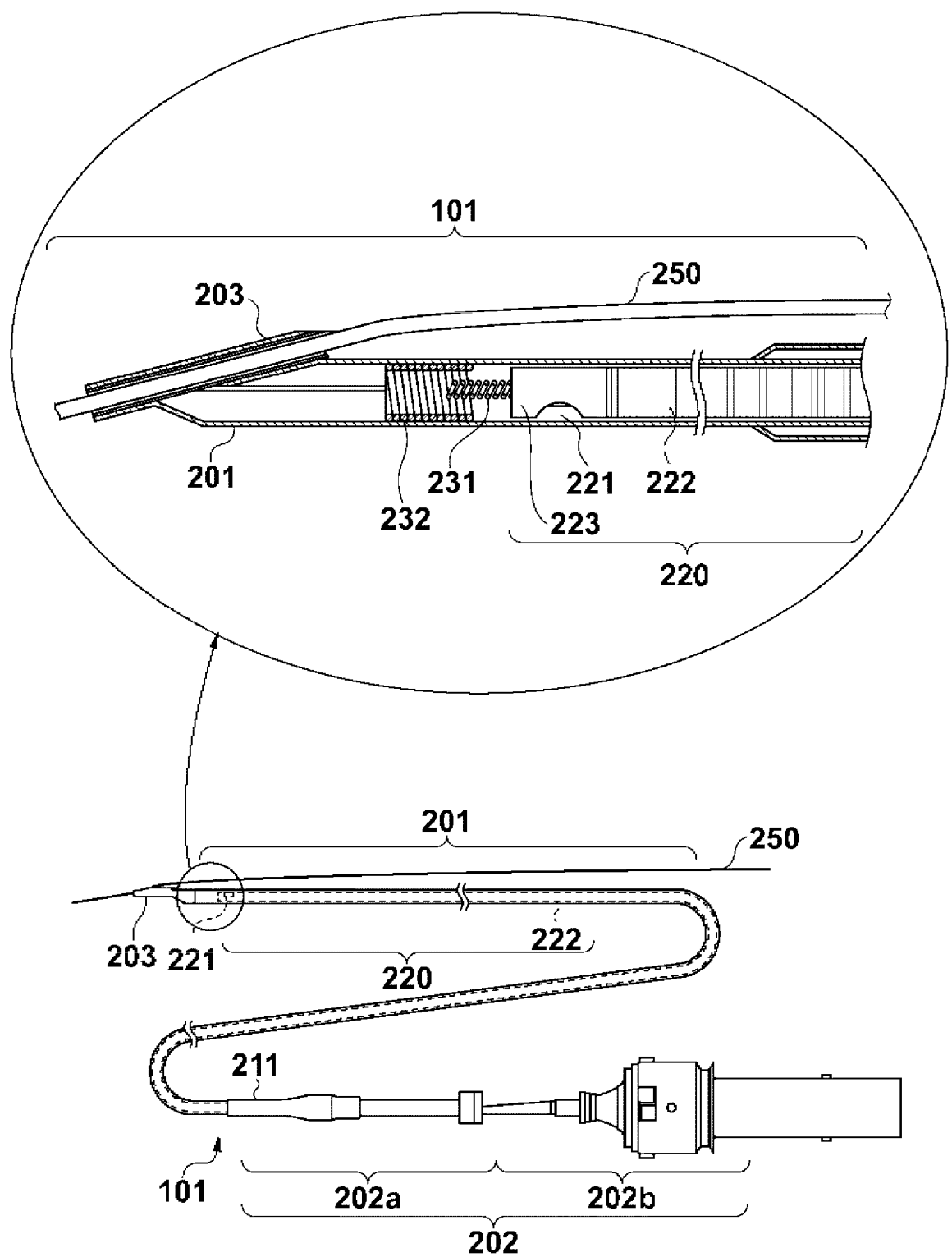
FIG. 2 is a diagram illustrating an overall constitution of a probe unit and a cross-sectional constitution of a distal end portion.

Subsequently, an overall constitution of the probe unit 101 and a cross-sectional constitution of a distal end portion will be described with reference to FIG. 2. As illustrated in FIG. 2, the probe unit 101 is constituted to include an elongated catheter sheath 201, which can be inserted into a blood vessel, and a connector portion 202 which can be disposed on a hand side of a user to be operated by the user without being inserted into a blood vessel. The distal end of the catheter sheath 201 is provided with a guide wire lumen tube 203, which fixes a guide wire 250 for guiding the probe unit 101 to the position of a blood vessel in a diagnostic target. The catheter sheath 201 forms a lumen, which continues from a portion connected to the guide wire lumen tube 203 to a portion connected to the connector portion 202.

Inside the lumen of the catheter sheath 201, an imaging core 220 including a transmitting and receiving unit 221 and a coiled drive shaft 222 is inserted through the catheter sheath 201 throughout substantially the overall length thereof. In the transmitting and receiving unit 221, the light transmitting and receiving unit for transmitting and receiving light is disposed. The drive shaft 222 is internally provided with an optical fiber cable and transfers a rotary drive force for rotating thereof.

The connector portion 202 can include a sheath connector 202a which is constituted to be unified to a proximal end of the catheter sheath 201, and a drive shaft connector 202b which is constituted to rotatably fix the drive shaft 222 to a proximal end of the drive shaft 222.

A kink-proof protector 211 is provided at a boundary portion between the sheath connector 202a and the catheter sheath 201. Accordingly, predetermined rigidity is maintained so as to be able to prevent bending (kink) occurring due to a rapid change of properties.

The proximal end of the drive shaft connector 202b is attached to the scanner and pull-back unit 102 in a freely detachable manner.

A housing 223 is a metallic pipe having a short cylindrical shape in which a notch portion is partially provided. The housing 223 is molded by performing carving from a metal ingot and metal powder injection molding (MIM). In addition, a short coiled elastic member 231 is provided on the distal end side of the housing 223.

The elastic member 231 is formed with a coiled stainless steel wire. Since the elastic member 231 is disposed on the distal end side, the imaging core 220 can be prevented from being caught inside the catheter sheath 201 when moving forward and rearward.

The reference numeral 232 indicates a reinforcement coil which is provided for the purpose of preventing sudden bending at the distal end portion of the catheter sheath 201.

The guide wire lumen tube 203 has a lumen for guide wire allowing the guide wire 250 to be inserted. The guide wire 250 can be used in order to introduce the distal end of the catheter sheath 201 to a target lesion.

Figure 3:
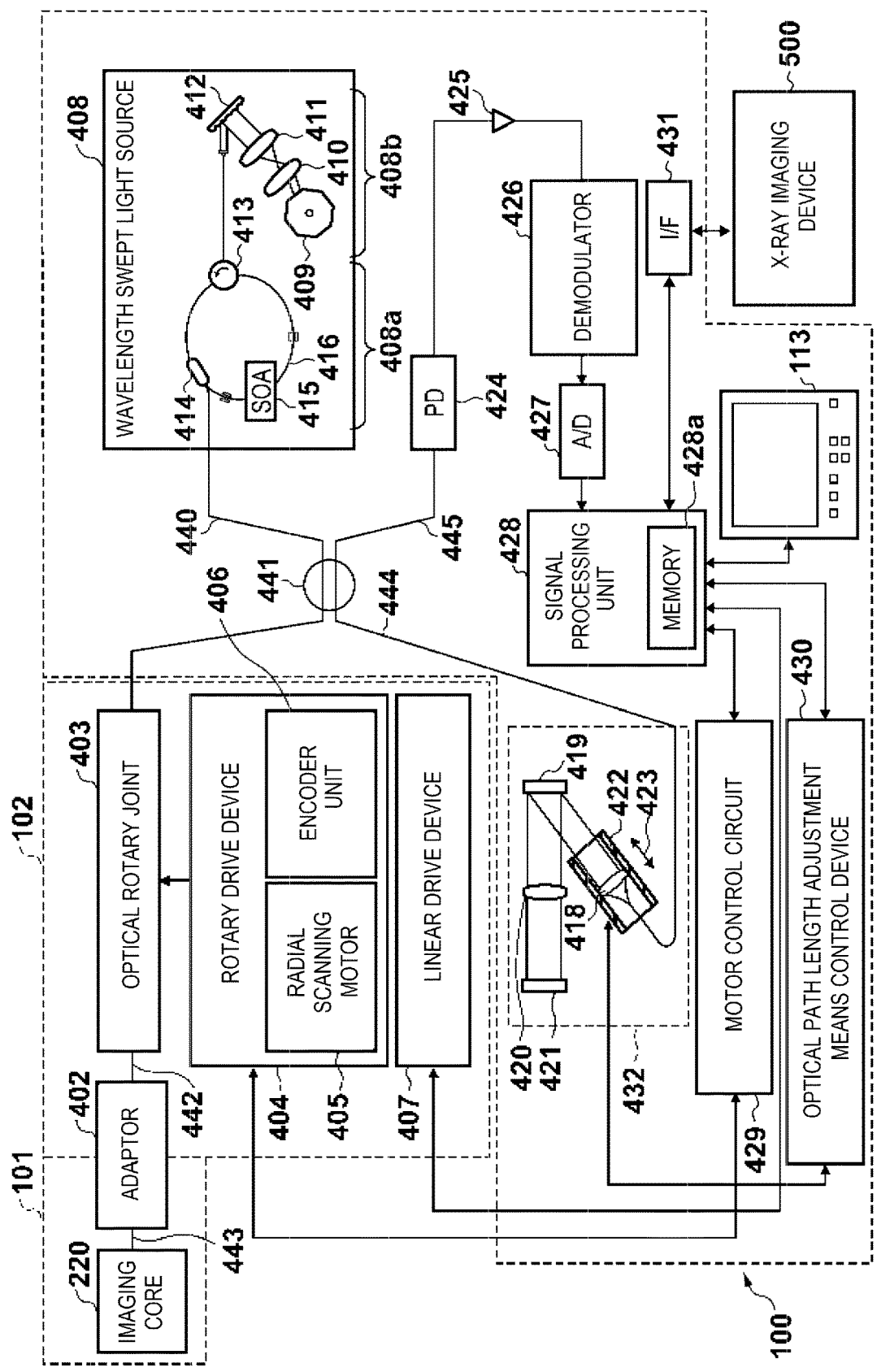
FIG. 3 is a diagram illustrating a functional constitution of the imaging apparatus for diagnosis.

Subsequently, a functional constitution of the imaging apparatus 100 for diagnosis will be described. FIG. 3 is a diagram illustrating the functional constitution of the imaging apparatus 100 for diagnosis having the function of the OCT (herein, a swept source OCT as an example). Hereinafter, a functional constitution of the swept source OCT will be described with reference to the same diagram.

In the diagram, the reference numeral 408 indicates a wavelength swept light source (swept laser), which is a type of an extended-cavity laser constituted of an optical fiber 416 coupled with a semiconductor optical amplifier 415 (SOA) in a ring shape, and a polygon scanning filter (408b).

Light output from the SOA 415 passes through the optical fiber 416 and enters the polygon scanning filter 408b. The light is subjected to wavelength selection herein, is amplified by the SOA 415, and is output from a coupler 414.

In the polygon scanning filter 408b, the wavelength is selected through a combination of a diffraction grating 412 which diffracts light, and a polygon mirror 409. In accordance with an exemplary embodiment, for example, the light diffracted by the diffraction grating 412 is concentrated on a surface of the polygon mirror 409 by using two lenses (410 and 411). Accordingly, only the light having a wavelength orthogonal to the polygon mirror 409 returns to the same optical path, thereby being output from the polygon scanning filter 408b. For example, in accordance with an exemplary embodiment, time sweeping of a wavelength can be performed by rotating the polygon mirror 409.

In the polygon mirror 409, for example, a 32-hedron mirror can be used and the number of rotations can be, for example, approximately 50,000 rpm. In accordance with an exemplary embodiment, high-speed and high-output wavelength sweeping through the wavelength swept source method can be performed in which the polygon mirror 409 and the diffraction grating 412 can be combined together.

Light of the wavelength swept light source 408 output from the coupler 414 is incident on one end of a first single mode fiber 440, thereby being transferred to the distal end side of the first single mode fiber 440. The first single mode fiber 440 can be optically coupled to a second single mode fiber 445 and a third single mode fiber 444 in a photo coupler unit 441 in the middle therebetween.

On the distal end side from the photo coupler unit 441 of the first single mode fiber 440, an optical rotary joint (a photo coupling portion) 403 which connects a non-rotary portion (fixed portion) and a rotary portion (rotary drive portion) with each other and transfers light is provided inside the rotary drive device 404.

In addition, on a distal end side of a fourth single mode fiber 442 in the optical rotary joint (the photo coupling portion) 403, a fifth single mode fiber 443 of the probe unit 101 is connected thereto via an adaptor 402 in a freely detachable manner. Accordingly, light from the wavelength swept light source 408 is transferred to the rotatably driven fifth single mode fiber 443, which is inserted through the inside of the imaging core 220.

Irradiation of the transferred light in rotary motion and axial motion can be performed with respect to a biological tissue in a blood vessel from the light transmitting and receiving unit 221 of the imaging core 220. A portion of the reflected light scattering on a surface or inside a biological tissue is collected by the light transmitting and receiving unit 320 of the imaging core 220, and returns to the first single mode fiber 440 side via the optical path in reverse. In addition, the portion of the reflected light moves to the second single mode fiber 445 side by the photo coupler unit 441 and is emitted from one end of the second single mode fiber 445. Thereafter, the portion of the reflected light is received by a photo detector (for example, a photo diode 424).

The rotary drive portion side of the optical rotary joint 403 is rotatively driven by a radial scanning motor 405 of the rotary drive device 404.

Meanwhile, an optical path length variable mechanism 432 for performing fine adjustment of the length of the optical path of the reference light is provided at the distal end on a side opposite to the photo coupler unit 441 of the third single mode fiber 444.

The optical path length variable mechanism 432 can include optical path length changing means for changing the length of the optical path corresponding to a fluctuation in the length of each probe unit 101 so as to be able to absorb the fluctuation in the length thereof when the probe unit 101 is replaced and used.

The third single mode fiber 444 and a collimating lens 418 can be provided on a one-axis stage 422 which is movable in the optical-axis direction thereof as indicated by the arrow 423, thereby forming the optical path length changing means.

In accordance with an exemplary embodiment, for example, the one-axis stage 422 functions as the optical path length changing means having a variable range of the optical path length as wide as the fluctuation in the length of the optical path of the probe unit 101 can be absorbed when the probe unit 101 is replaced. Moreover, the one-axis stage 422 can also include a function as adjustment means for adjusting an offset. For example, when the distal end of the probe unit 101 is not in close contact with a surface of a biological tissue, a state of being interfered with the reflected light from the surface position of the biological tissue can be set by performing fine changing of the length of the optical path through the one-axis stage.

The length of the optical path is subjected to fine adjustment through the one-axis stage 422, and light reflected by a mirror 421 via a grating 419 and a lens 420 is mixed with light obtained from the first single mode fiber 440 side in the photo coupler unit 441 which is provided in the middle of the third single mode fiber 444, thereby being received by the photo diode 424.

The interference light received by the photo diode 424 as described above is subjected to photoelectric conversion, thereby being input to a demodulator 426 after being amplified by the amplifier 425. The demodulator 426 performs demodulation processing of extracting only a signal portion of the interference light, and an output thereof is input to an A/D converter 427 as an interference light signal.

In the A/D converter 427, the interference light signal can be sampled, for example, at 90 MHz at as many as 2,048 points, for example, thereby generating digital data (interference light data) for one line. The sampling frequency is set to 90 MHz on the premise that approximately 90% of a periodical cycle (12.5 μsec) of the wavelength sweeping is extracted as digital data at 2,048 points when a repetition frequency of the wavelength sweeping is set to, for example, 40 kHz. However, the sampling frequency is not particularly limited thereto.

The interference light data generated by the A/D converter 427 in a line unit is input to the signal processing unit 428. The signal processing unit 428 generates data (line data) in a depth direction by causing the interference light data to be subjected to frequency resolution through fast fourier transform (FFT). Then, the generated data is subjected to coordinate conversion so as to construct a cross-sectional image at each position in a blood vessel, thereby outputting the constructed image to the LCD monitor 113.

Furthermore, the signal processing unit 428 is connected to an optical path length adjustment means control device 430. The signal processing unit 428 controls a position of the one-axis stage 422 via the optical path length adjustment means control device 430.

The processing of the signal processing unit 428 can be realized as a predetermined program is installed in an embedded system and executed.

Moreover, the imaging apparatus 100 for diagnosis of the embodiment can include an interface (I/F) 431 connecting an X-ray imaging device 500 as illustrated. The imaging apparatus 100 for diagnosis can acquire an image of the heart of the examinee in real time from the X-ray imaging device 500 via the interface 431.

In the above-described constitution, when a user operates the operation control device 103 and inputs an instruction to start scanning, the signal processing unit 428 controls the scanner and pull-back unit 102 so as to rotate the imaging core 220 and to pull the imaging core 220 at a predetermined velocity, thereby performing a movement in a blood vessel in the longitudinal direction. In this case, in order to prevent the imaging core 220 emitting and receiving light from being hindered by blood, a transparent flushing liquid is generally caused to flow inside a blood vessel. As a result and described above, the A/D converter 427 outputs digital interference light data, and the signal processing unit 428 stores the data in a memory 428a. Then, the signal processing unit 428 constructs cross-sectional images of each position along the imaging core 220 in the movement direction, from the data stored in the memory 428a.

Figure 4:
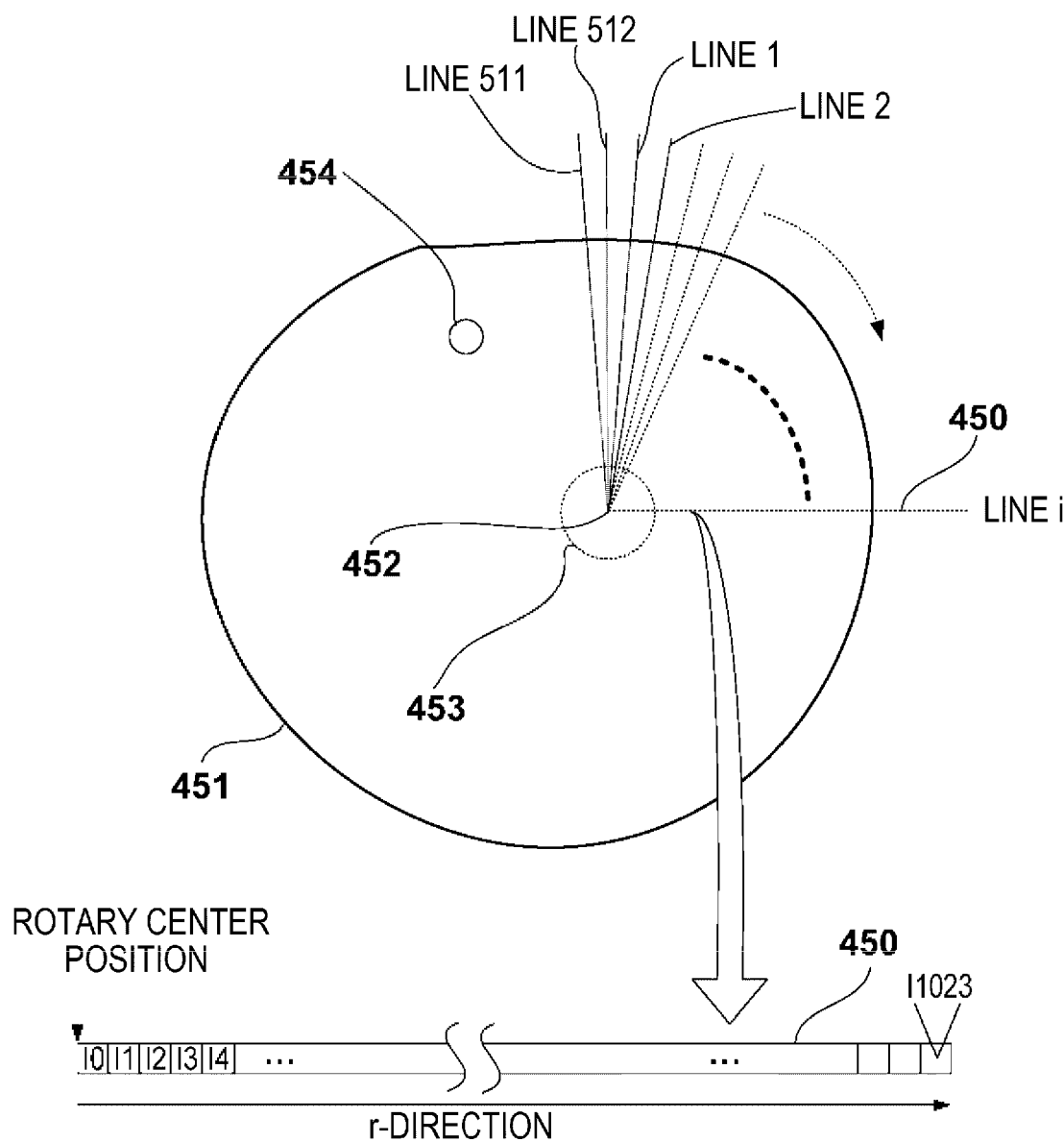
FIG. 4 is a diagram for illustrating reconstruction processing of a cross-sectional image.

Here, processing related to generation of one cross-sectional image will be described with reference to FIG. 4. FIG. 4 is a diagram for illustrating reconstruction processing of the cross-sectional image of a blood vessel 451 in which the imaging core 220 is positioned. The measurement light is transmitted and received for multiple times while the imaging core 220 makes one rotation (rotates 360 degrees). As transmission and reception of light are performed once, data of one line in the direction in which irradiation of the light is performed can be obtained. Therefore, for example, when transmission and reception of light are performed 512 times during one rotation, 512 items of the line data radially extending from a rotary center 452 can be obtained. As the line data is subjected to the known computation, the vascular cross-sectional image oriented in the radial direction (r-direction) from the rotary center position can be generated. One line of the vascular cross-sectional image is constituted of 1024 brightness values from I0 to I1023. I0 is the brightness value of the rotary center position, and I1023 is the brightness value of a farthest position away from the rotary center position.

In this manner, 512 items of the line data are constructed. However, 512 items of the line data are close to one another in the vicinity of the rotary center position and are estranged from one another as being away from the rotary center position. Therefore, regarding the pixels in the empty space of each line, known interpolation processing is performed so as to generate an image, and thus, the cross-sectional image can be generated, which can be visually recognized by a person. Note that, the center position of the cross-sectional image coincides with the rotary center position of the imaging core 220 but is not the center position of the vascular cross section.

Since there is reflection of the catheter sheath 201 itself when performing transmission and reception of light, a shadow 453 of the catheter sheath 201 is formed in the cross-sectional image as illustrated. In addition, the reference numeral 454 in the diagram indicates the shadow of the guide wire 250. Actually, the guide wire 250 is made of metal and does not allow light to transmit therethrough. Therefore, an image of the rear side portion (when seen from the rotary center position) of the guide wire 250 cannot be obtained. In accordance with an exemplary embodiment, the illustration is a conceptual diagram.

When a user operates the operation control device 103 and inputs an instruction to start scanning, the signal processing unit 428 controls the scanner and pull-back unit 102 so as to rotate the imaging core 220 and to pull the imaging core 220 at a predetermined velocity, thereby performing a movement in a blood vessel in the longitudinal direction (the pull-back processing). As a result, the signal processing unit 428 receives the line data of each rotary angle and the data is stored in the memory 428a. Then, when the pull-back processing ends, the line data stored in the memory 428a is processed so as to form a plurality of the cross-sectional images, and the images are stored in the memory 428a again. Moreover, the images can be connected in series, thereby constructing a three-dimensional model of a blood vessel lumen in the memory 428a.

Figure 7:
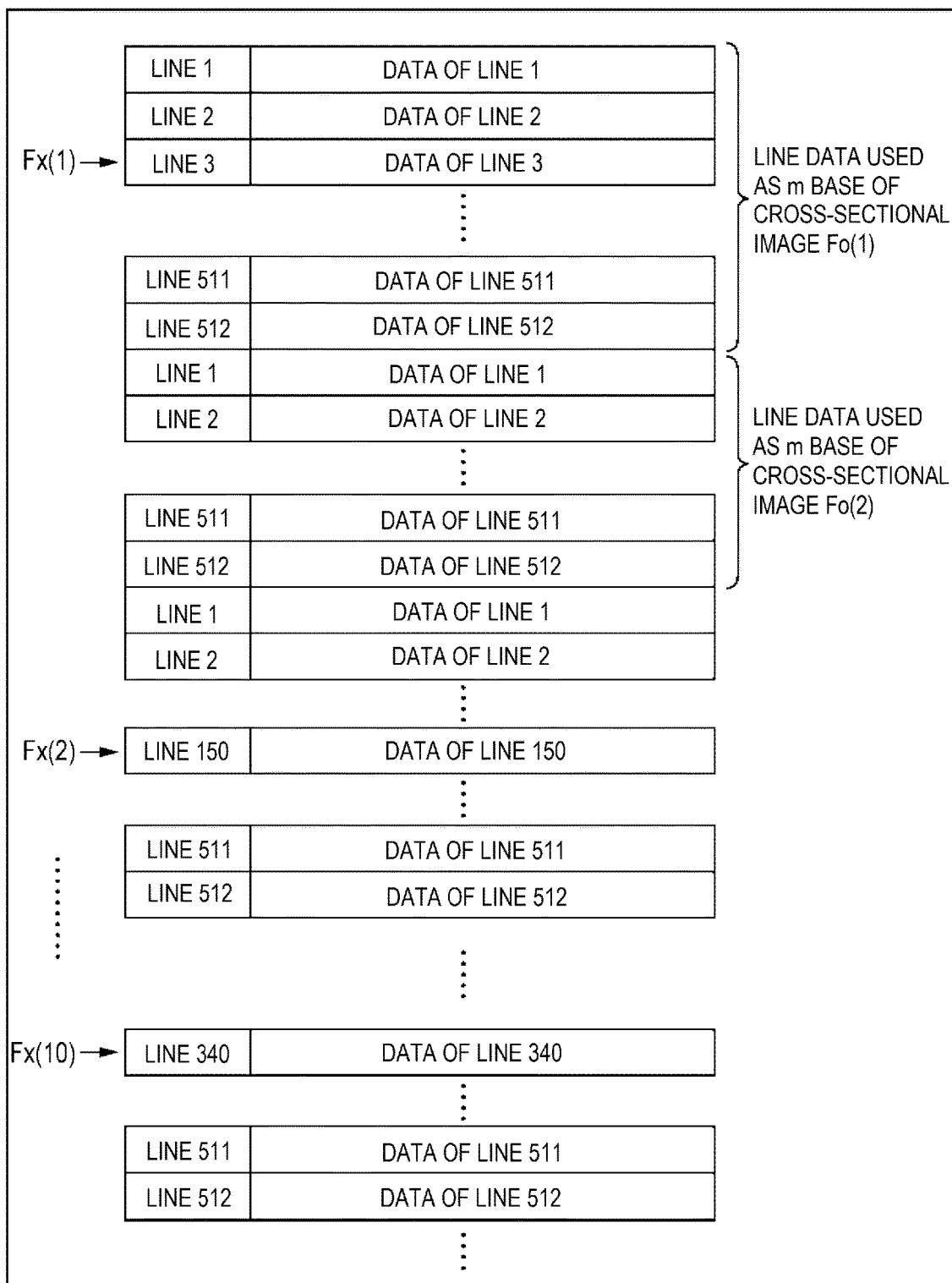
FIG. 7 is a diagram for illustrating synchronization between storage data, which becomes a base of a tomographic image and the X-ray image in an exemplary embodiment.

FIG. 7 shows a storage state of the line data stored in the memory 428a through the pull-back processing. The embodiment describes an example in which one vascular cross-sectional image is constructed by using 512 items of the line data. If the rotational velocity of the imaging core 220 is, for example, 9,600 rpm and the time taken for the pull-back is five seconds, the imaging core 220 makes 800 rotations (=9,600/60×5) during the time thereof. Since 512 items of the line data can be obtained in one rotation, approximately 400,000 items of the line data are stored in the memory 428a.

Figure 5:
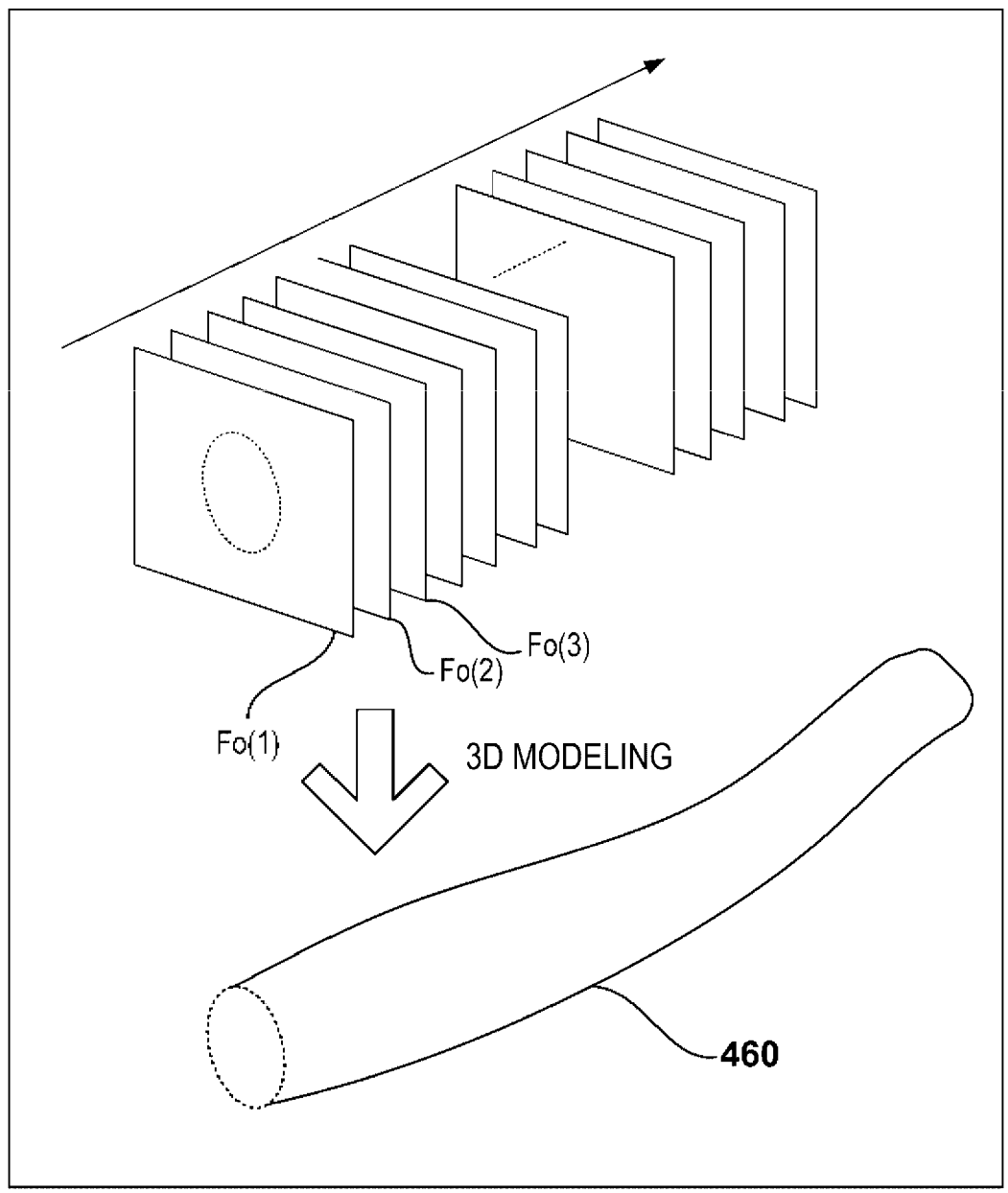
FIG. 5 is a diagram illustrating an example of reconstructed three-dimensional model data of a blood vessel.

Fo (1), Fo (2), Fo (3), and so on in FIG. 5 respectively indicate the vascular cross-sectional images each of which is constructed so as to have 512 items of the line data as a unit, in the line data illustrated in FIG. 7. Then, as the vascular cross-sectional images Fo (1), Fo (2), Fo (3), and so on are connected in series, and a three-dimensional model 460 can be constructed.

The diagnostic target of the embodiment is the coronary artery (or the coronary vein). Since the coronary artery is positioned so as to surround the heart, the coronary artery itself also moves (vibrates) due to an influence of a cardiac beat of the heart. In the imaging apparatus for diagnosis of the embodiment, the imaging core 220 is positioned in a blood vessel, and the cross-sectional images of the blood vessel are constructed from the data, which can be obtained through the pull-back processing in which the imaging core 220 rotates and moves. Therefore, an influence of a cardiac beat can be avoided.

The sequence of the vascular cross-sectional images Fo (1), Fo (2), Fo (3), and so on in FIG. 5 is a positional order of a blood vessel in the axial direction and is a chronological order as well. Therefore, during the pull-back scanning, the vascular cross-sectional image at the timing when there is a cardiac beat is in a misaligned state with respect to the vascular cross-sectional image at the timing when there is no influence of a cardiac beat, and is in disorder. Then, the three-dimensional model exhibits the disorder.

In the present exemplary embodiment, when the three-dimensional model 460 is visualized and displayed, a site in disorder due to an influence of a cardiac beat and a site not in disorder are displayed in an easily discriminable manner. As a result thereof, a user (for example, a doctor) can be prevented from erroneously diagnosing the site as an abnormal vascular site.

In order to solve the problem, there is a need to detect the timing when there is a cardiac beat. In the present exemplary embodiment, the X-ray imaging device 500 can detect the cardiac beat and obtain the detection timing. In order to obtain the timing of cardiac beat detection, the vascular cross-sectional image and the X-ray image need to be synchronized. Here, first, synchronization thereof will be described, and thereafter, cardiac beat detection will be described.

The X-ray imaging device 500 of the embodiment images the heart of the examinee and outputs 30 items of the X-ray image data per second, for example, while having the viewpoint position is fixed. In the following description, 30 items per second is exemplified. However, the quantity can be changed to 15 items per second and the like by setting the X-ray imaging device 500. The embodiment of the present disclosure can perform the processing regardless of the setting of the X-ray imaging device 500. Therefore, the embodiment is not particularly limited thereto. The imaging apparatus 100 for diagnosis of the embodiment sequentially stores the X-ray image data from the X-ray imaging device 500 in the memory 428a via the interface 431 at least during the pull-back processing.

The vascular cross-sectional images are expressed as Fo (1), Fo (2), and so on. In order to be distinguished therefrom, hereinafter, the X-ray images stored in chronological order are expressed as Fx (1), Fx (2), and so on.

As described above, since the imaging core 220 rotates at a velocity of 9,600 rpm, the imaging core 220 can make 160 rotations per second, that is, 160 pseudo vascular cross-sectional images are imaged per second. Meanwhile, since the X-ray imaging device 500 images 30 X-ray images per second, approximately five vascular cross-sectional images can be constructed while imaging one X-ray image, in simple calculation.

Here, regarding the method of synchronization therebetween in the embodiment, after the pull-back processing starts and while each item of the line data obtained based on optical coherence is stored in the memory 428a, when one X-ray image Fx (i) (i=1, 2, and so on) is acquired from the X-ray imaging device 500 via the interface 431, the timing when the X-ray image Fx (i) starts to be acquired is caused to correspond to the line data of that timing. FIG. 7 illustrates that the X-ray image Fx (1) is stored in the memory 428a via the interface 431 when the line data of a line 3 in the first rotation is stored.

As a result there above, when the signal processing unit 428 reconstructs the vascular cross-sectional image Fo (1) based on the line data stored in the memory 428a, the line data can include the line data of the timing when the X-ray image Fx (1) is acquired. Therefore, it is possible for the signal processing unit 428 to consider that the vascular cross-sectional image Fo (1) and the X-ray image Fx (1) are the images obtained at the same timing, thereby performing processing. In accordance with an exemplary embodiment, for example, synchronization between the vascular cross-sectional image and the X-ray image can be achieved.

FIG. 7 illustrates an example in which one item of the line data is individually caused to correspond to the X-ray image. However, it is acceptable as long as accuracy at which one vascular cross-sectional image corresponds to the X-ray image is achieved. Since 512 items of the line data utilized when constructing one vascular cross-sectional image can be obtained in 1/160 seconds (=6.25 msec), it is sufficient when accuracy is achieved as the time accuracy for the timing of starting acquisition of one X-ray image. In addition, the synchronization is not limited to the above-described example. For example, when the X-ray image Fx (i) is received, information may be retained so as to indicate which optical coherence data in series is received.

Figure 6:
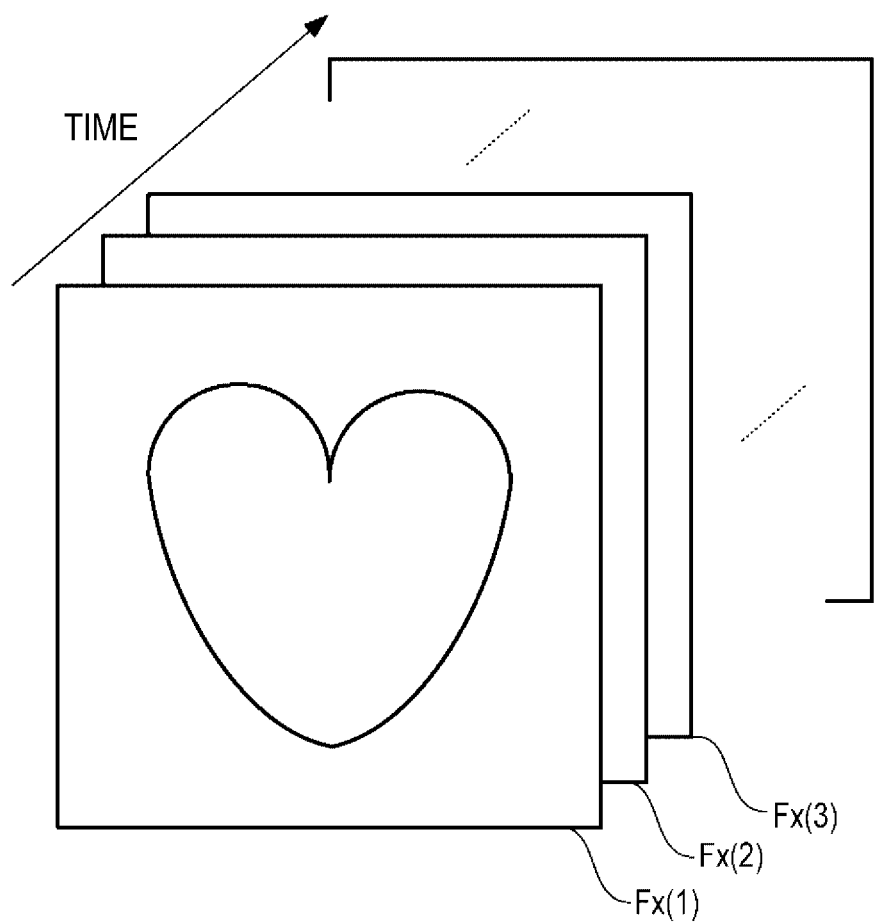
FIG. 6 is a diagram for illustrating an example of a two-dimensional X-ray image of an exemplary embodiment.

Subsequently, determination of the presence and the absence of a cardiac beat will be described. The X-ray imaging device 500 of the embodiment outputs the X-ray images of the heart of the examinee at the velocity of 30 items per second at the fixed viewpoint. When the X-ray images obtained after the timing when the pull-back processing starts are expressed as Fx (1), Fx (2), Fx (3), and so on, the memory 428a stores the X-ray images as illustrated in FIG. 6.

A cardiac beat can be considered to be variation in form with respect to the time axis of the heart. Therefore, the presence and the absence of a cardiac beat can be determined by whether the correlation is high or low between two X-ray images of the heart which are adjacent to each other on the time basis. When the correlation between the two adjacent X-ray images is relatively high, it denotes that the difference between the two adjacent images is small. In addition, when the correlation between the two adjacent X-ray images is relatively low, it denotes that the difference between the two adjacent images is relatively significant. In the embodiment, a mutual difference between the two X-ray images adjacent to each other on the time basis is expressed in numerical form, the difference and a threshold value are compared to each other, and the degree of dissimilarity is determined, thereby determining the presence and the absence of a cardiac beat.

When the X-ray image which is presently targeted is considered to be Fx (i), the X-ray image one before thereof (before 1/30 seconds) can be expressed as Fx (i−1). In addition, when xmax represents the number of pixels of the X-ray image in the horizontal direction, ymax represents the number of pixels thereof in the vertical direction, and Fx (i, x, y) represent the pixel values of the coordinates (x, y) in the ith X-ray image, dissimilarity D of the target X-ray image Fx (i) with respect to the X-ray image Fx (i−1) which is one before thereof may be obtained through the following expression.

$$D(i)=\Sigma\Sigma\{Fx(i,x,y)-Fx(i-1,x,y)\}^2$$

Here, $\Sigma\Sigma$ represents a sum total when the variables x and y are respectively varied within a range of 1 to xmax and 1 to ymax.

Then, when the dissimilarity D (i) and a threshold value Th set in advance are compared to each other, resulting in a relationship of D (i)>Th, it denotes that the target X-ray image is significant in variation (small in correlation) compared to the X-ray image immediately before thereof, and the target X-ray image is determined to be significantly influenced by a cardiac beat.

As described above, since the X-ray image and the vascular cross-sectional image can be synchronized together, a portion significantly influenced by a cardiac beat and a portion less influenced thereby in the three-dimensional model of a blood vessel can be specified. However, as described above, there is a need to note that the X-ray image and the vascular cross-sectional image are different from each other in the number of items which can be obtained per unit time.

Here, it is determined that an influence of a cardiac beat is significant within the range from the X-ray images Fx (10)

to Fx (20). In this case, when the vascular cross-sectional image Fo (100) is synchronized with the X-ray image Fx (10), and Fo (155) is synchronized with the X-ray image Fx (20), it is determined that the influence of a cardiac beat is significant within the range of a section from the vascular cross-sectional images Fo (100) to Fo (155). In accordance with an exemplary embodiment, for example, the two vascular cross-sectional images respectively corresponding to the X-ray images positioned at both ends of the section which is determined to be significant in cardiac beat are specified, thereby determining a range interposed between the two vascular cross-sectional images as the section which is significantly influenced by a cardiac beat.

Hereinbefore, descriptions are given regarding the principle in determining the site significantly influenced by a cardiac beat and the site less influenced thereby in the three-dimensional model of the embodiment obtained from the vascular cross-sectional images.

Figure 10:
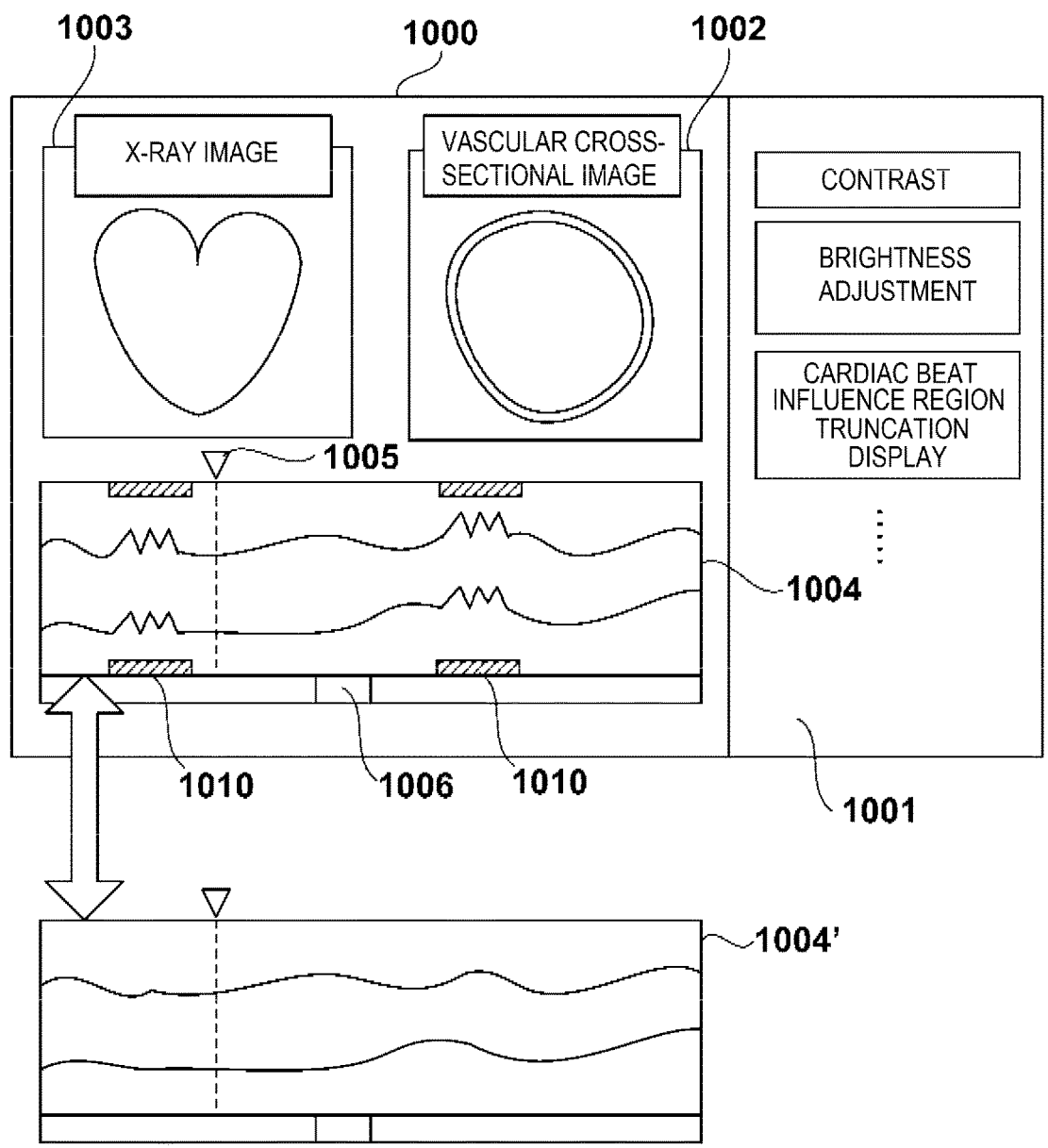
FIG. 10 is a diagram illustrating an example of a user interface displayed in a display screen of the imaging apparatus for diagnosis in an exemplary embodiment.

FIG. 10 illustrates an example of a user interface 1000, which can be displayed in the LCD monitor 113 after the pull-back processing is performed.

The user interface 1000 can include a display region 1001 in which various types of instruction buttons are disposed for a user so as to make an instruction, a display region 1002 displaying a vascular cross-sectional image on a plane orthogonal to the vascular axis, a display region 1003 displaying the X-ray image, and a display region 1004 displaying the cross-sectional image when the three-dimensional model of a blood vessel is cut on a plane along the vascular axis. The display region 1004 displays a variable marker 1005 of which a position is variable by using the mouse 114. In addition, a scroll bar 1006 for performing scrolling in the horizontal direction is also provided in a lower portion of the display region 1004.

The display region 1002 displays the vascular cross-sectional image (the cross-sectional image on a plane vertical to the vascular axis) which corresponds to the broken line portion indicated by the position of the marker 1005. In addition, the display region 1003 displays the X-ray image, which can be imaged at the timing when the imaging core 220 is at the position of the marker 1005. The X-ray image has an imaging time interval greater than that of the vascular cross-sectional image. Therefore, in accordance with an exemplary embodiment, the display region 1002 displays the X-ray image, which can be imaged at the time nearest to the time shown by the position, which the marker 1005 indicates.

As the characteristic point of the embodiment, in order to emphasize the section in the display region 1004 which is determined to be influenced by a cardiac beat, discrimination bars (or marks) 1010 are disposed at the upper end and the lower end in the horizontal axis (the pull-back direction of the imaging core 220) as illustrated. In accordance with an exemplary embodiment, a user can find a section having a cardiac beat in the display. Therefore, one can relatively easily determine whether or not the disorder in the section is an influence of a cardiac beat.

Moreover, in the present embodiment, considering that reliability is low in an image of the section having a cardiac beat, for example, in an image of the section in which the movement of the X-ray image is significant, a display mode can be provided for truncating the section displayed by the bar 1010. When using this mode, it can be desirable to recognize the level of the section having particularly significant activity so as to truncate the section having significant activity. The method of realizing thereof will be described below. The mode is realized by clicking the button of "cardiac beat influence region truncation display" which is positioned on the right side in the diagram. As the button is clicked, the display region 1004 is switched to a display region 1004' as illustrated at the lower portion in the diagram. When the mode is switched to the display region 1004', one image on the bar 1010 is truncated from the left end to the right end, and an image immediately adjacent to the left side from the left end of the bar 1010 and an image immediately adjacent to the right side from the right end of the bar 1010 are connected together, thereby performing processing of adding a display so as to recognize the position through which the connected position can be confirmed (truncation processing). When shifted to the display region 1004', the sign "cardiac beat influence region truncation display" of the button is switched to "cardiac beat influence region display". As a user operates the mouse and clicks the button of the sign, the display region 1004' returns to the display region 1004 again.

Figure 8:
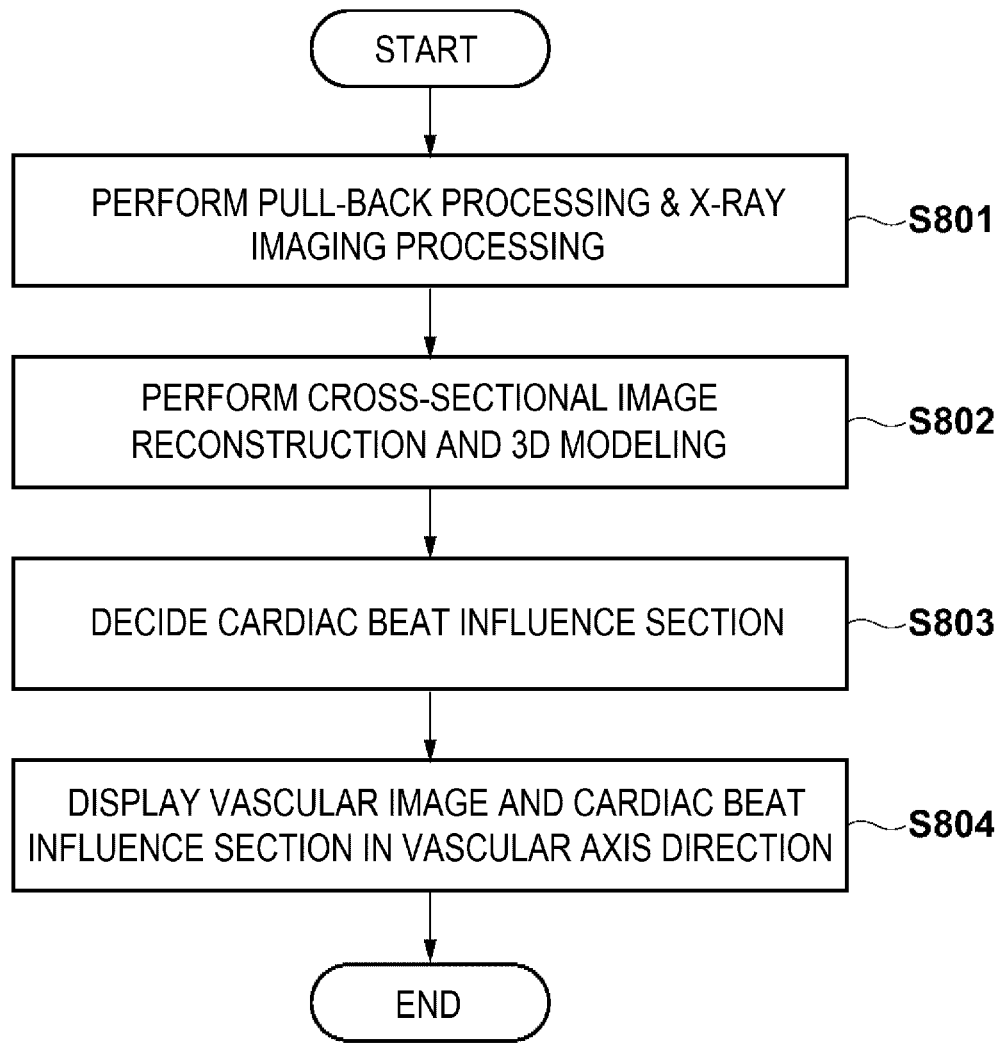
FIG. 8 is a flow chart illustrating a procedure of processing of an exemplary embodiment.
Figure 9:
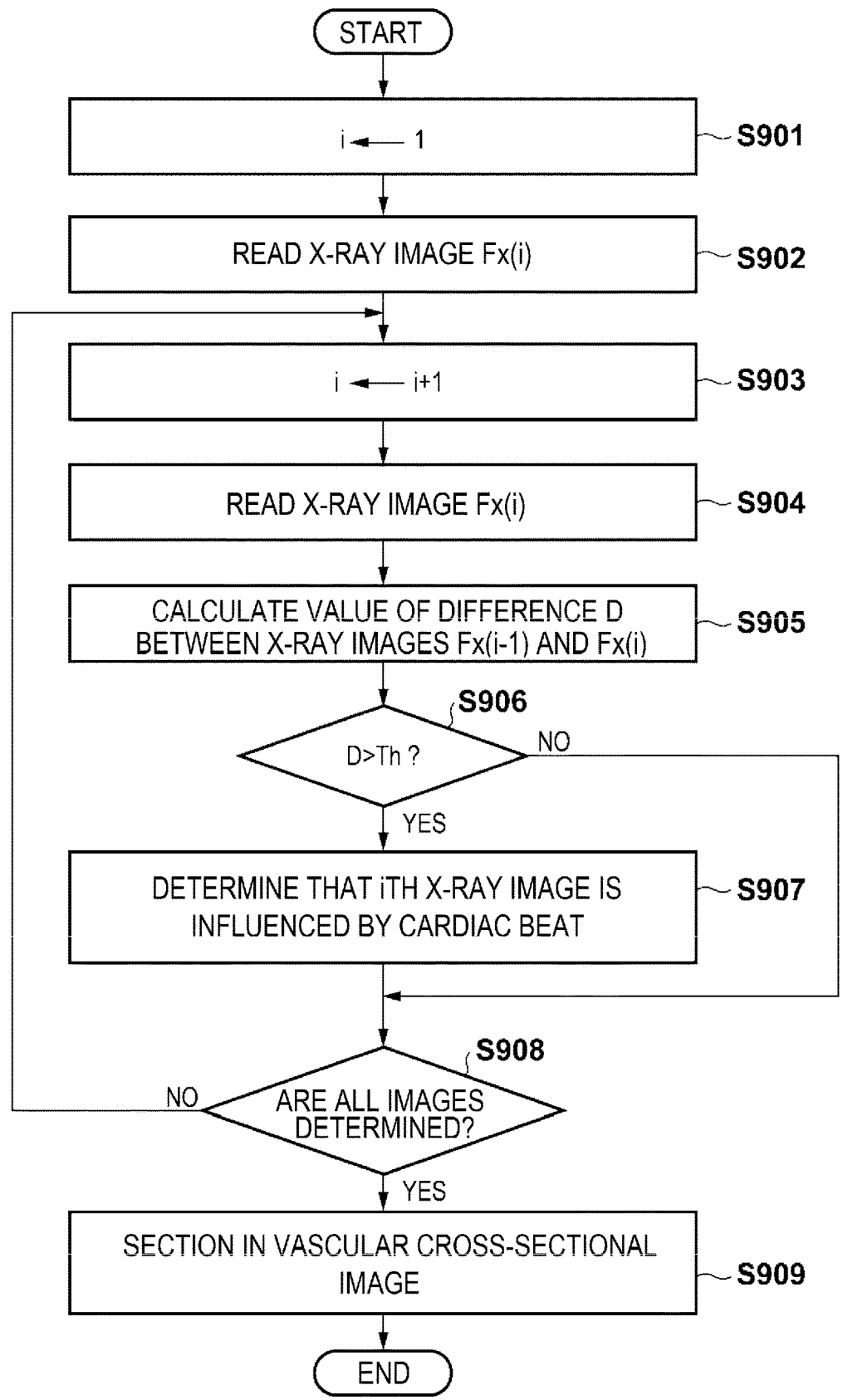
FIG. 9 is a flow chart illustrating detailed processing of FIG. 8 deciding a cardiac beat influence section.

Hereinafter, a procedure of processing of the signal processing unit 428 will be described with reference to the flow charts in FIGS. 8 and 9. The program in the procedure of processing according to the flow charts in FIGS. 8 and 9 is stored in a hard disk device or the like (not illustrated). In addition, the processing is performed when a catheter is positioned in the coronary artery of a patient, and a pull-back instruction is made through the operation panel 112.

As the pull-back instruction is made, in Step S801, the signal processing unit 428 causes the imaging core 220 to rotate at a predetermined velocity, while performing pulling processing at a predetermined velocity. Thus, while optical coherent line data is stored in the memory 428a, the X-ray images transferred from the X-ray imaging device 500 are also stored in the memory 428a. In this case, in order to achieve synchronization between the optical coherent line data and the X-ray image, as illustrated in FIG. 7, every time one X-ray image is acquired, information indicating that the corresponding X-ray image is acquired is added to the line data at the timing of starting acquisition thereof.

In this manner, when the pull-back processing ends, the processing proceeds to Step S802, thereby performing processing of constructing the cross-sectional image of the rotation plane of the imaging core 220 based on the received line data, and generating the three-dimensional model of the vascular lumen surface by connecting the images in series.

Thereafter, in Step S803, the X-ray image influenced by a cardiac beat is specified based on the X-ray image, thereby specifying the section in which the X-ray images influenced by a cardiac beat continue, in the group of the X-ray images which continue in time series. Then, when one section is targeted, two vascular cross-sectional images corresponding to two X-ray images at the position on both ends of the section are specified, thereby making a decision as the section in which an influence of a cardiac beat is significant between the two vascular cross-sectional images.

Then, in Step S804, a composite result of the cross-sectional image of the three-dimensional model along the vascular axis generated as described above, and the image indicating the section which is determined to be influenced by a cardiac beat is displayed (refer to FIG. 10).

Subsequently, descriptions will be given with reference to the flow chart in FIG. 9 regarding the processing in which the X-ray image influenced by a cardiac beat is obtained from the X-ray images stored in the memory 428a in Step S803 described above, thereby obtaining the corresponding vascular cross-sectional image. As is clear from the descriptions above, note that, the X-ray images Fx (1), Fx (2), and so on which continue in time series are stored already in the memory 428*a*.

First, in Step S901, the signal processing unit 428 resets the variable i for specifying the X-ray image to "1", and in Step S902, the signal processing unit 428 reads the X-ray image Fx (i) (=Fx (1)) from the memory 428*a*.

Subsequently, in Step S903, the variable i is increased by "1", and in Step S904, the X-ray image Fx (i) is read. Note that, two X-ray images Fx (i) and Fx (i−1) which continue in time series are read at this time.

Subsequently, in Step S905, the difference D between two images is calculated. Repeatedly, the following expression is used.

$$D=\Sigma\Sigma\{Fx(i,x,y)-Fx(i-1,x,y)\}^2$$

Then, in Step S906, the difference D and the threshold value Th are compared to each other. In a case of D>Th, in Step S907, variation of the target X-ray image Fx (i) is greater than that of the X-ray image Fx (i−1) immediately before thereof, thereby being considered to be influenced by a cardiac beat. Therefore, the value which is indicated by the current variable i is stored in the memory region prepared in advance.

Then, in Step S908, processing after Step S903 is repeated until it is judged that all the X-ray images are determined.

In this manner, as the determination processing for all the X-ray images ends, the processing proceeds to Step S909, thereby deciding the section of the vascular cross-sectional image which is determined to be significantly influenced by a cardiac beat, from the group in which the numbers of the X-ray images which are determined to be significantly influenced by a cardiac beat through the above-described determination processing continue in series. For example, as the group in which the numbers of the X-ray images which are determined to be significantly influenced by a cardiac beat continue in series, {3, 4, 5, 6, 7}, {31, 32, 33, 34, 35}, and so on are found.

Since two X-ray images Fx (3) and Fx (7) at both ends in the first group are known, if the vascular cross-sectional images synchronized therewith are searched for the data in FIG. 7, two corresponding vascular cross-sectional images can be found, thereby determining that the section therebetween as the section which is significantly influenced by a cardiac beat. In a case of the second group, the vascular cross-sectional images corresponding to the X-ray images Fx (31) and Fx (35) are searched.

Specifying of the section of the vascular cross-sectional image significantly influenced by a cardiac beat is equivalent to the specification of the section of the three-dimensional model in the vascular axis direction. Therefore, similar processing may be performed with respect to the group of the continuous X-ray images.

As described above, according to the present embodiment, a section significantly influenced by a cardiac beat is displayed in the cross-sectional image (the image displayed in the display region 1004 of FIG. 10) along the vascular axis of a blood vessel in a discriminable manner. As a result thereof, for example, even a relatively inexperienced doctor can relatively easily discriminate whether or not an unnatural vascular site is caused due to an influence of a cardiac beat.

In the embodiment described above, the vascular cross-sectional images are connected in series so as to generate a 3D model, and the cross-sectional images along the vascular axis are reconstructed. However, the present disclosure is not limited thereto. For example, the image along the vascular axis can be reconstructed by simply connecting line images of a vertical line (without being limited to the vertical line, it is acceptable as long as the line images are in the same direction) passing through the pixels at the center (the rotary center position of the imaging core 220 as well) of each of the cross-sectional images orthogonal to the vascular axis. As a result thereof, processing can be more simplified compared to a case of reconstructing a 3D model, and thus, rendering processing can be sped up.

Figure 11A:
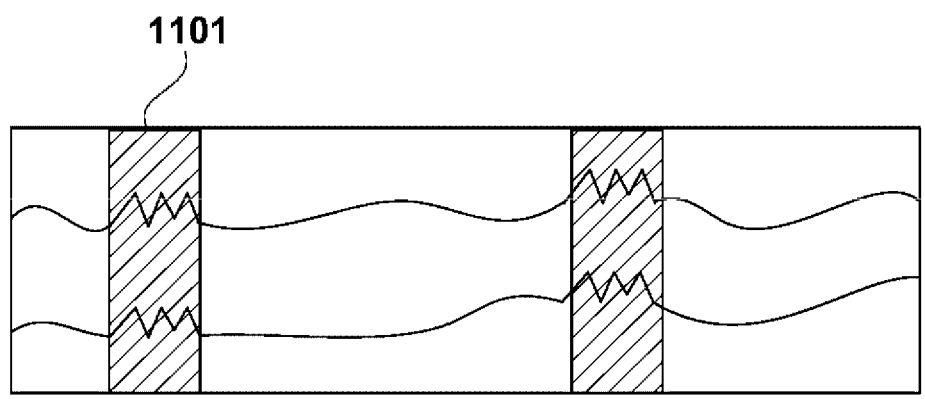
FIG. 11A is a diagram illustrating an example of another display form of a cross section of the blood vessel in an axial direction in accordance with an exemplary embodiment.

In the embodiment described above, descriptions are given regarding the example in which the bars indicating the section significantly influenced by a cardiac beat are disposed at the upper end and the lower end of the display region so as to interpose the cross-sectional image along the vascular axis of a blood vessel. However, the embodiment is not limited thereto. That is, it is acceptable as long as the section significantly influenced by a cardiac beat and the section having no influence can be discriminated from each other. Therefore, as illustrated in FIG. 11A, an image 1101 in the section significantly influenced by a cardiac beat may be displayed in color or density different from that of other images.

Figure 11B:
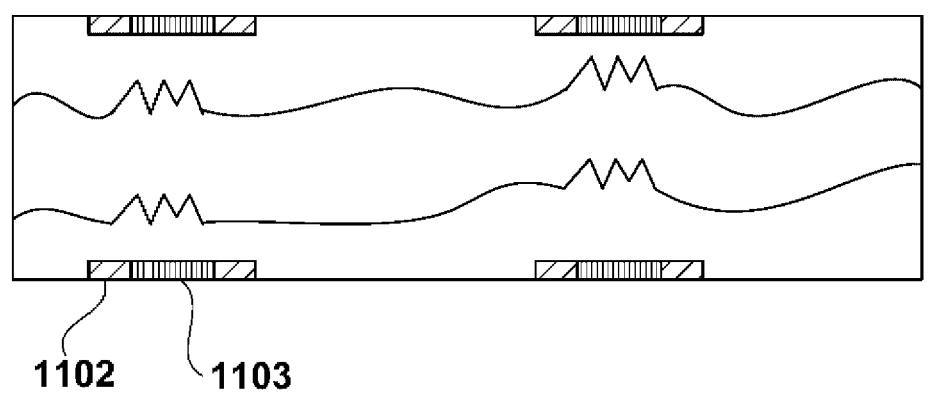
FIG. 11B is a diagram illustrating an example of further another display form of the cross section of the blood vessel in the axial direction in accordance with an exemplary embodiment.

In addition, in the embodiment, the influence of a cardiac beat is classified into two types such as a significant grade and a small grade. However, determination can be made in three-grade scale such as a significant grade, an intermediate grade, and a small grade in an influence of a cardiac beat by providing two threshold values. Moreover, determination can be made in multi-grade scale which is subdivided further by setting more threshold values. For example, when performing three-grade evaluation, as illustrated in FIG. 11B, a section 1102 in which an influence of a cardiac beat is intermediate and a section 1103 in which an influence of a cardiac beat is significant so as to be discriminated from each other can be displayed. In a case of FIG. 11B, the display button for truncating the cardiac beat influence region is prepared as many as the number corresponding to the number of the grade in scale. In accordance with an exemplary embodiment, for example, a button for truncating the region in which an influence of a cardiac beat is equal to or greater than the intermediate grade, and a button for truncating the region in which an influence of a cardiac beat is equal to or greater than the significant grade may be respectively prepared.

In addition, in the embodiment, the section having or not having an influence of a cardiac beat is displayed (the bar 1010 and the like) by utilizing the cross-sectional image along the vascular axis. However, the present disclosure is not limited only thereto and can be constituted as follows.

As disclosed above, a user can freely change the position of the marker 1005. In accordance with an exemplary embodiment, the marker 1005 indicates not only the position of the physical space along the vascular axis but also allows to see the indicated position of the time axis, as described. Therefore, determining the position of the marker 1005 instructed by a user is in the cardiac beat influence region is equivalent to determining the timing when the imaging core is positioned at the position of the marker 1005 instructed by a user is in the time interval having an influence of a cardiac beat. Therefore, the display form of the display region 1002 may be switched depending on the timing when the imaging core is positioned at the position instructed by using the marker 1005 is in the time interval having an influence of a cardiac beat or out of the time interval. There are several examples of switching the display form. For example, the frame color of the display region 1002 may be switched. As an example thereof, the frame color of the display region 1002 is displayed in red when the position of the marker 1005 is in the time interval having an influence of a cardiac beat, and the frame color of the display region 1002 is displayed in white when the position is out of the time interval thereof. In addition, in a case where the influence of a cardiac beat is subdivided into multi-grade scale, the frame color may be changed for each of the grades. In addition, regarding switching of the display form of the display region 1002, the color of the character string "vascular cross-sectional image" of the index may be changed instead of the frame. Depending on the cases, a display of the background color of the display region 1002 may be switched.

As described above, naturally, switching of the display form of the display region 1002 and displaying of the presence and the absence of the cardiac beat influence region in the display region 1004 may be performed at the same time.

Hereinbefore, the embodiments have been described. In the embodiments, the example in which a vascular tomographic image is used in an optical coherence apparatus for diagnosis has been described. However, the embodiments can be applied to an ultrasound apparatus for diagnosis or an apparatus having both thereof. Therefore, the present disclosure is not limited to only the optical apparatus for diagnosis as described above.

As described above, reconstruction of the cross-sectional image and reconstruction processing of the cross-sectional image in the vascular axis direction can be performed by the signal processing unit 428 which is constituted of a micro-processor. Since the micro-processor functions by executing the program, the program is included in the scope of the present disclosure as well. In addition, generally, the program is stored in a computer readable storage medium such as CD-ROM, DVD-ROM, or the like, and the program is set to a reading device (a CD-ROM drive or the like) included in the computer, thereby being executable by being copied or installed in the system. Therefore, the computer readable storage medium can be included in the scope of the present disclosure as well.

The present disclosure is not limited to the embodiments described above, and thus, various changes and modifications can be made without departing from the gist and the scope of the present disclosure. Therefore, in order to make the scope of the present disclosure to be in public, the following claims are attached herein.

The detailed description above describes imaging apparatus for diagnosis, method of controlling the same, program, and computer readable storage medium. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An imaging apparatus for diagnosis acquiring information of an inside of a blood vessel and reconstructing a vascular image, the imaging apparatus comprising:
    an imaging core configured to emit light or ultrasound toward a lumen surface of a blood vessel of an examinee and to detect reflection of the light or ultrasound;
    a probe configured to accommodate the imaging core;
    a motor configured to rotate the imaging core and to move the imaging core along the probe at a predetermined velocity;
    an X-ray imaging device configured to continuously acquire X-ray images of the examinee along a time axis while acquiring the information of the inside of the blood vessel by performing the rotation and the movement of the imaging core;
    a processor configured to:
        specify a vascular-activity occurrence X-ray image based on a degree of correlation of an adjacent X-ray image with respect to the time axis of the X-ray images acquired by the X-ray imaging device;
        determine a corresponding position of the moving imaging core for imaging timing of the vascular-activity occurrence X-ray image; and
        generate an axially-directed cross-sectional image along the vascular axis based on the information acquired through the rotation and the movement of the imaging core; and
    a display configured to display a composite result of the axially-directed generated cross-sectional image and an image showing the corresponding position of the moving imaging core for imaging timing of the vascular-activity occurrence X-ray image.

2. The imaging apparatus for diagnosis according to claim 1, wherein the processor is further configured to:
    generate an instruction regarding a position in a vascular axis direction in the axially-directed cross-sectional image which is displayed by the display; and
    wherein the display is configured to display a vascular cross-sectional image on a plane orthogonal to a vascular axis at the position in the vascular axis direction, and the vascular-activity occurrence X-ray image acquired at timing when the imaging core is positioned at the position in the vascular axis direction.

3. The imaging apparatus for diagnosis according to claim 2, wherein the processor is configured to:
    determine whether or not the timing when the imaging core is positioned at the position in the vascular axis direction is vascular-activity occurrence timing; and
    switch a display form of a radially-directed cross-sectional image in accordance with a determination result of whether or not the imaging core is positioned at the position in the vascular axis direction is the vascular-activity occurrence timing.

4. The imaging apparatus for diagnosis according to claim 3, wherein the processor is configured to:
    switch any one of a frame color, an index color, and a background color for displaying the radially-directed cross-sectional image, based on the timing when the imaging core is positioned at the position in the vascular axis direction is the vascular-activity occurrence timing.

5. The imaging apparatus for diagnosis according to claim 1, wherein when Fx (i) represents an ith target X-ray image in imaged sequence and Fx (i, x, y) represent pixel values of coordinates (x, y) in a target X-ray image, the processor is configured to compute the following expression to obtain dissimilarity between the target X-ray image and an X-ray image immediately before the target X-ray image:
    D (i)=$\Sigma\Sigma\{Fx (i, x, y) - Fx (i-1, x, y)\}^2$, $\Sigma\Sigma$ represents a sum total of computation results for all the coordinates; and
    when dissimilarity D (i) and a threshold value Th set in advance are compared to each other resulting in a relationship of D (i)>Th, it is determined that the vascular activity occurs in the target X-ray image Fx (i).

6. The imaging apparatus for diagnosis according to claim 1, wherein the processor is configured to:
generate a display excluding a vascular-activity occurrence site on the display; and
delete an image at the position determined from axially-directed cross-sectional images, and display truncated images after deletion of the image.

7. The imaging apparatus for diagnosis according to claim 1, wherein the processor is configured to:
generate an image mark displayed at the vascular-activity occurrence site in the axial direction of the axially-directed cross-sectional image.

8. The imaging apparatus for diagnosis according to claim 7, wherein the image mark shows a degree of magnitude of activity to be displayed at the vascular-activity occurrence site in the axial direction of the axially-directed cross-sectional image.

9. The imaging apparatus for diagnosis according to claim 1, wherein the processor is configured to:
generate a vascular-activity occurrence region in the axial direction of the axially-directed cross-sectional image, and wherein the vascular-activity occurrence region is displayed in color or a density different from the color or a density of a region having no vascular-activity occurrence.

10. The imaging apparatus for diagnosis according to claim 1, wherein the X-ray imaging device is configured to acquire the X-ray images of a heart of the examinee in real time.

11. A method of controlling an imaging apparatus for diagnosis acquiring information of an inside of a blood vessel and reconstructing a vascular image by using an imaging core configured to emit light or ultrasound toward a lumen surface of a blood vessel and to detect reflection of the light or ultrasound, a probe configured to accommodate the imaging core, and a motor configured to rotate the imaging core and to move the imaging core along the probe at a predetermined velocity, the method comprising:
continuously acquiring X-ray images of the examinee along a time axis while acquiring the information of the inside of the blood vessel by performing the rotation and the movement of the imaging core;
specifying a vascular-activity occurrence X-ray image based on a degree of correlation of an adjacent X-ray image with respect to the time axis of the X-ray vascular-activity occurrence image which is acquired by the X-ray image acquisition step;
determining a corresponding position of the moving imaging core for imaging timing of the vascular-activity occurrence X-ray image which is specified by the specification step;
generating the axially-directed cross-sectional image along the vascular axis based on the information acquired through the rotation and the movement of the imaging core; and
displaying a composite result of the axially-directed cross-sectional image which is generated by the generation step and an image which shows the corresponding position determined by the determination step on a display of the moving imaging core for imaging timing of the vascular-activity occurrence X-ray image.

12. The method according to claim 11, comprising:
generating an instruction regarding a position in a vascular axis direction in the axially-directed cross-sectional image which is displayed by the display, and
displaying a vascular cross-sectional image on a plane orthogonal to a vascular axis at the position in the vascular axis direction, and the vascular-activity occurrence X-ray image acquired at timing when the imaging core is positioned at the position in the vascular axis direction.

13. The method according to claim 12, comprising:
determining whether or not the timing when the imaging core is positioned at the position in the vascular axis direction is vascular-activity occurrence timing; and
switching a display form of a radially-directed cross-sectional image in accordance with a determination result of whether or not the imaging core is positioned at the position in the vascular axis direction is the vascular-activity occurrence timing.

14. The method according to claim 13, comprising:
switching any one of a frame color, an index color, and a background color for displaying the radially-directed cross-sectional image, based the timing when the imaging core is positioned at the position in the vascular axis direction is the vascular-activity occurrence timing.

15. A non-transitory computer readable storage medium which is read and executed by a processor included in an imaging apparatus for diagnosis to cause the processor to execute each of the steps according to claim 11.

16. An imaging apparatus for diagnosis acquiring information of an inside of a blood vessel and reconstructing a vascular image, the imaging apparatus comprising:
an imaging core configured to emit light or ultrasound toward a lumen surface of a blood vessel of an examinee and to detect reflection of the light or ultrasound;
a probe configured to accommodate the imaging core;
a motor configured to rotate the imaging core and to move the imaging core along the probe at a predetermined velocity;
an X-ray imaging device configured to continuously acquire X-ray images of the examinee along a time axis while acquiring the information of the inside of the blood vessel by performing the rotation and the movement of the imaging core;
a processor configured to:
specify a vascular-activity occurrence time interval based on a degree of correlation of an adjacent X-ray image with respect to the time axis of the X-ray images acquired by the X-ray imaging device;
generate a plurality of radially-directed cross-sectional images orthogonal to a vascular axis at each of the positions along the vascular axis based on the information acquired through the rotation and the movement of the imaging core; and
determine whether or not timing when the imaging core is positioned at the position on the vascular axis of one of the plurality of radially-directed cross-sectional images is within the vascular-activity occurrence time interval; and
a display configured to display a radially-directed cross-sectional image in a display form in accordance with a result of whether or not the imaging core is positioned at the position on the vascular axis of the one of the plurality of the radially-directed cross-sectional images.

17. The imaging apparatus for diagnosis according to claim 16, wherein the processor is configured to:
generate an instruction regarding a position in a vascular axis direction in the axially-directed cross-sectional image which is displayed by the display; and
wherein the display is configured to display a vascular cross-sectional image on a plane orthogonal to the vascular axis at the position-in the vascular axis direction, and an X-ray image acquired at timing when the imaging core is positioned at the position in the vascular axis direction.

18. The imaging apparatus for diagnosis according to claim 17, wherein the processor is configured to:
   determine whether or not the timing when the imaging core is positioned at the position in the vascular axis direction is vascular-activity occurrence timing; and
   switch a display form of a radially-directed cross-sectional image in accordance with a determination result of whether or not the imaging core is positioned at the position in the vascular axis direction is the vascular-activity occurrence timing.

19. The imaging apparatus for diagnosis according to claim 18, wherein the processor is configured to:
   switch any one of a frame color, an index color, and a background color for displaying the radially-directed cross-sectional image, based on the timing when the imaging core is positioned at the position in the vascular axis direction is the vascular-activity occurrence timing.

20. The imaging apparatus for diagnosis according to claim 16, wherein the processor is configured to:
   generate a display excluding a vascular-activity occurrence site on the display; and
   delete an image at the position determined from axially-directed cross-sectional images, and display truncated images after deletion of the image.

* * * * *